United States Patent [19]

Sone et al.

[11] Patent Number: 4,479,866
[45] Date of Patent: Oct. 30, 1984

[54] GAS SENSOR WITH SENSITIVE ELEMENT ENCLOSED IN PERFORATED HOOD

[75] Inventors: Kohki Sone, Tokyo; Hatsuo Nagaishi, Zushi; Hidehiro Minami, Yokohama; Kenji Okamura, Zushi; Yoshitaka Kitagasaki, Yokosuka, all of Japan

[73] Assignee: Nissan Motor Company, Limited, Yokohama, Japan

[21] Appl. No.: 537,549

[22] Filed: Oct. 3, 1983

Related U.S. Application Data

[63] Continuation of Ser. No. 299,599, Sep. 4, 1981, abandoned.

[30] Foreign Application Priority Data

Oct. 17, 1980 [JP] Japan .................. 55-145277

[51] Int. Cl.³ .................................. G01N 27/58
[52] U.S. Cl. ........................ 204/425; 204/426
[58] Field of Search ............ 204/426, 428, 15, 425; 73/23; 123/440, 489; 60/276

[56] References Cited

U.S. PATENT DOCUMENTS

| | | | |
|---|---|---|---|
| 3,928,161 | 12/1975 | McIntyre et al. | 204/428 |
| 4,184,934 | 1/1980 | Bode et al. | 204/428 |
| 4,222,840 | 9/1980 | Murphy et al. | 204/426 |
| 4,224,113 | 9/1980 | Kimura et al. | 204/1 T |
| 4,240,893 | 12/1980 | Hamano | 204/428 |
| 4,290,586 | 9/1981 | Kane et al. | 266/80 |
| 4,310,401 | 1/1982 | Stahl | 204/428 |

FOREIGN PATENT DOCUMENTS 2304359 8/1974 Fed. Rep. of Germany ... 204/195 S

Primary Examiner—G. L. Kaplan
Attorney, Agent, or Firm—Schwartz, Jeffery, Schwaab, Mack, Blumenthal & Koch

[57] ABSTRACT

A gas sensor, e.g. oxygen sensor of the solid electrolyte concentration cell type, having a gas-sensitive element comprising a plate-shaped substrate fixed to an end portion of the sensor body and a laminate of relatively thin layers. A hollow cylindrical protective hood is attached to the sensor body to enclose the sensitive element therein, and two or more openings are formed in the cylindrical wall of the hood to allow a gas subject to measurement to flow into the interior of the hood and flow out. To avoid direct exposure of the sensitive element, which exhibits directionality in its output characteristics with regard to the gas flow through said openings, each of said openings is located between the sensitive element and the free end of the hood such that a cross-sectional plane intersecting the openings does not intersect the sensitive element.

1 Claim, 26 Drawing Figures

GAS SENSOR WITH SENSITIVE ELEMENT ENCLOSED IN PERFORATED HOOD

This application is a continuation of application Ser. No. 299,599, filed Sept. 4, 1981 and now abandoned.

BACKGROUND OF THE INVENTION

This invention relates to a gas sensor having a sensitive element in the form of a laminate of relatively thin layers on a plate-shaped substrate which is enclosed in a generally cylindrical hood formed with gas inlet and outlet openings.

Currently various kinds of gas sensors are used in many fields. For example, in the automobile industry it has been popular to use either an oxygen sensor or a carbon dioxide sensor in an air-fuel ratio control system as a means for producing a feedback signal indicative of an actual air-fuel ratio of a gas mixture supplied to the engine.

In most cases the sensitive part of such a gas sensor has a layer of either a solid electrolyte or a semiconductive metal oxide as the essential element of the sensor with the provision of some other layers such as electrode and shield layers, and it is a recent trend to construct the sensitive part in the form of a laminate of relatively thin layers on a substrate to thereby reduce the size of the sensor and enhance the sensitivity. For practical reasons such as the ease of production, it is usual to use a plate-shaped substrate so that the sensitive part as a whole becomes generally plate-like.

In a practical gas sensor, the plate-shaped sensitive part or element is fixed to one end of a sensor body, and a hollow cylindrical hood is attached to the sensor body so as to enclose the sensitive element therein for the purpose of protecting the sensitive element from shocks or collisions during handling and also from high temperatures and high flow velocities of gases subject to measurement. To allow a portion of a gas subject to measurement to come into contact with the sensitive element, two or more openings in the form of slits or holes are formed in the cylindrical side wall of the hood. With a view to maintaining good responsiveness of the sensitive element, these openings are located such that the gas which flows into the interior of the hood collides directly against the sensitive element. In other words, a cross-sectional plane bisecting the openings intersects the senstive element.

In general, the output characteristic of a plate-shaped gas-sensitive element exhibits some changes as the orientation of the element with respect to the direction of the flow of a gas subject to measurement varies. That is, the element exhibits directionality. For example, we have recognized that, when an oxygen sensor having a plate-shaped sensitive element is employed in the aforementioned air-fuel ratio control system, the accuracy of the control depends to some extent on the orientation of the oxygen-sensitive element with respect to the direction of the flow of exhaust gas at the location where the sensor is disposed. From a practical point of view, it constitutes a significant inconvenience that the sensor must be installed in the exhaust system in a particular orientation.

SUMMARY OF THE INVENTION

The present invention is concerned with a gas sensor of the type having a sensitive element in the form of a laminate of relatively thin layers on a plate-shaped substrate which is enclosed in a generally hollow cylindrical protective hood formed with gas inlet and outlet openings. It is a primary object of the invention to solve the above described problem that the output characteristic of the sensitive element varies as the orientation of the sensitive element with respect to the direction of the flow of a gas subject to measurement varies.

The gist of the invention is to form the gas inlet and outlet openings in the hood at such locations that the gas flowing into the interior of the hood does not collide directly against the sensitive element.

A gas sensor according to the invention comprises a body adapted for attachment of the sensor to a separate apparatus through which a gas subject to measurement is flowing, a sensitive element having a plate-shaped substrate and a laminate of a plurality of relatively thin layers including at least one layer of a gas-sensitive material is formed on a major surface of the substrate, and a generally hollow cylindrical hood which is fixed to the sensor body such that the sensitive element is enclosed in the hood and is entirely spaced from the inner side of the hood and is formed with at least two openings in the cylindrical wall thereof to allow a portion of the gas flowing in the aforementioned apparatus to flow into the interior of the hood and then flow out. This gas sensor is characterized in that each of the aforementioned openings in the wall of the hood is located between the sensitive element and the free end of the hood in a direction longitudinal of the hood such that any plane cross-sectional of the hood and intersecting at least one of the openings does not intersect the sensitive element.

In this gas sensor, the gas flowing into the interior of the hood through any of the openings in the cylindrical wall of the hood comes into contact with the laminate part of the gas-sensitive element after repeated collisions against, and reflections on, the inner surface of the cylindrical hood and, therefore, in a state well mixed and relatively low in flow velocity. For this reason, the sensitive element exhibits a practically constant output characteristic irrespective of its orientation with respect to the direction of flow of the gas outside the hood.

Preferably, the openings in the cylindrical wall of the hood are in the form of either circumferential arc-shaped slits or circular holes arranged such that the center points of all the slits or holes are contained in a plane cross-sectional of the hood.

These, as well as other objects and advantages of the present invention, will become apparent upon consideration of the following written description of the invention together with the drawings or may be learned by practice of the invention defined in the appended claims.

DESCRIPTION OF THE PREFERRED EMBODIMENTS

Figure 1:
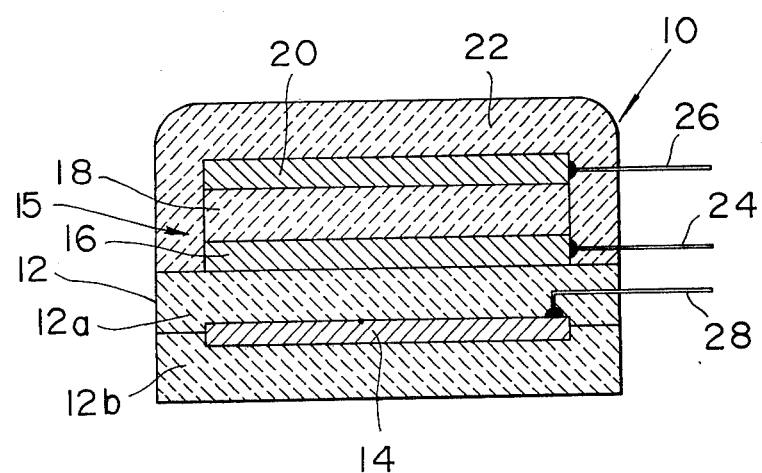
FIG. 1 is a schematic and sectional view of an oxygen-sensitive element for use in an oxygen sensor according to the invention.

FIG. 1 shows a known oxygen-sensitive element 10 which works on the principle of oxygen concentration cell and can be used in an exhaust line of an automotive internal combustion engine. A structurally basic member of this element 10 is a base plate or substrate 12 made of a ceramic material such as alumina. A concentration cell part 15 of the oxygen-sensitive element 10 takes the form of a laminate of relatively thin, film-like layers. More in detail, an inner electrode layer 16 often called reference electrode layer is formed on a major surface of the substrate 12, and a layer 18 of an oxygen ion conductive solid electrolyte such as zirconia stabilized with a minor amount of yttria is formed on the same side so as to closely and substantially entirely cover the inner electrode layer 16. An outer electrode layer 20 often called measurement electrode layer is laid on the outer surface of the solid electrolyte layer 18. Platinum is a typical example of suitable materials for the outer electrode layer 20. Essentially, these three layers 16, 18, 20 constitute the concentration cell part. For example, the thickness of the solid electrolyte layer 18 is about 50 microns or smaller, and each of the two electrode layers 16 and 20 is as thin as about 5 microns. Each of these three layers 16, 18, 20 can be formed by a physical vapor deposition technique or by applying a paste containing a powdered electrode material or solid electrolyte material onto the surface of the substrate 12 or the underlying layer and sintering the powdered material contained in the applied paste. The substrate 12 may be about 6 mm × 10 mm in width and 1–2 mm in thickness by way of example.

Usually the outer surfaces of the concentration cell part 15 of this element 10 are coated with a protecting layer 22, which is formed of a ceramic material and has a porous structure to allow a gas subject to measurement to pass therethrough.

An electric heater element 14 is embedded in the substrate 12 because the conductivity of oxygen ions in the solid electrolyte layer 18 becomes very low when the temperature of the element 10 is below a certain level. In practice, the substrate 12 may be prepared by face-to-face bonding of two alumina sheets 12a and 12b one of which is precedingly provided with the heater element 14 in the form of, for example, a platinum wire or a thin platinum layer formed through printing of a platinum paste and sintering of the platinum powder contained in the printed paste.

The concentration cell part 15 of this oxygen-sensitive element 10 generates an electromotive force when there is a difference in oxygen partial pressure between the outer electrode side and the inner electrode side of the solid electrolyte layer 18. To sense the concentration of oxygen in a gas to which the outer electrode layer 20 is exposed through pores in the protecting coating layer 22, there is the need of establishing a reference oxygen partial pressure at the interface between the solid electrolyte layer 18 and the inner electrode layer 16. According to U.S. Pat. Nos. 4,207,159 and 4,224,113, the reference oxygen partial pressure is produced by so forming the solid electrolyte layer 18 as to be microscopically porous and externally supplying a DC current of an adequate intensity to the concentration cell part 15 so as to flow through the solid electrolyte layer 18 between the two electrode layers 16 and 20. An oxygen partial pressure of a suitable magnitude can be maintained at the interface between the inner electrode 16 and the solid electrolyte 18 as a joint effect of migration of oxygen ions through the solid electrolyte layer 18 caused by the flow of the aforementioned current and diffusion of oxygen molecules through the pores in the solid electrolyte layer 18. In this case a suitable material for the inner electrode layer 16 is platinum or its alloy. Another method of establishing a reference oxygen partial pressure in the concentration cell part 15 is to use an electronically conducting mixture of a certain metal and its oxide, such as Ni-NiO, as the material of the inner electrode layer 16. In this case the solid electrolyte layer 18 is made to have a tight and practically gas-impermeable structure.

The oxygen-sensitive element 10 of FIG. 1 is provided with three lead wires 24, 26 and 28. The lead 24 is connected to the inner electrode layer 16 and the lead 26 to the outer electrode layer 20 in order to supply the aforementioned DC current to the concentration cell part 15 and also to take out an electromotive force the cell 15 generates. The lead 28 is connected to the heater 16 to supply a heating current, and, though not shown in FIG. 1, the lead 26 is connected to the heater 14 too so as to serve as a ground lead common to the concentration cell 15 and the heater 14. Of course it is optional to provide a separate ground lead (not shown) to the heater 14 instead of connecting the lead 26 to the heater 14.

In practical applications, the oxygen-sensitive element of FIG. 1 must be assembled with supporting and casing parts to give an oxygen sensor unit that can be attached to, for example, an exhaust manifold of an automotive engine.

Figure 2:
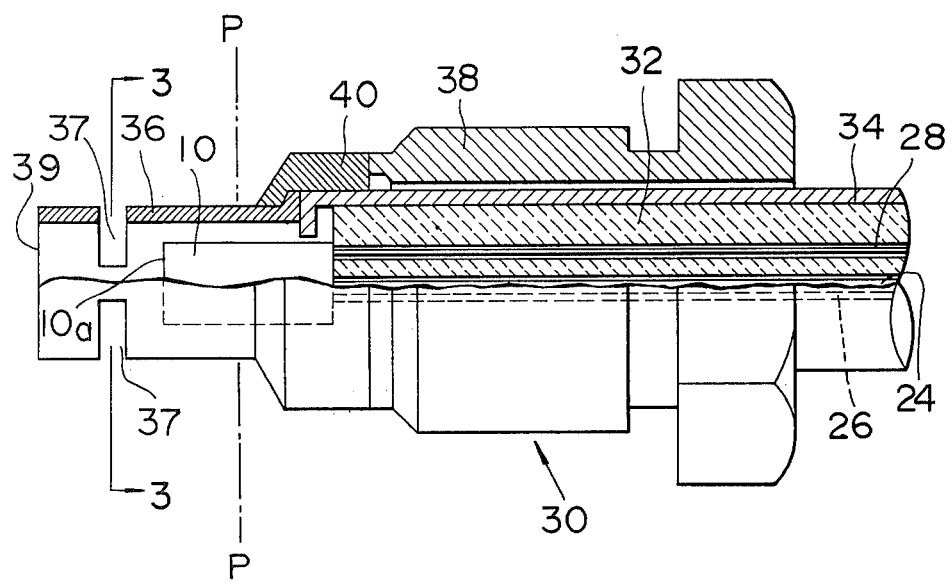
FIG. 2 is a partly sectional side elevation view of an oxygen sensor as an embodiment of the invention.
Figure 3:
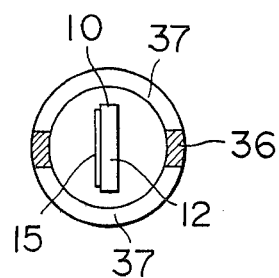
FIG. 3 is a cross-sectional view taken along the line 3—3 in FIG. 2.

FIGS. 2 and 3 show an oxygen sensor 30 which embodies the present invention and includes the oxygen-sensitive element 10 of FIG. 1. The oxygen-sensitive element 10 is fixedly mounted on an end face of a cylindrical rod 32, which is made of a ceramic material such as alumina and formed with three axial holes (no numerals) through which the leads 24, 26, 28 of the element 10 are extended, respectively. The ceramic rod 32 is tightly inserted into a tubular holder 34 made of a metal such as stainless steel, and a generally tubular metal body 38 having a threaded section and a nut-shaped section is fixed to the outer side of the holder 34. A hollow cylindrical hood 36 made of stainless steel is substantially coaxially fixed to the forward end of the tubular holder 34 so as to enclose the oxygen-sensitive element 10 therein. To firmly support the hood 36, a retainer ring 40 is welded to both the outer surface of a forward end portion of the holder 34 and the outer surface of an end portion of the hood 36. The inner side of the hood 36 is entirely spaced from the outer surfaces of the oxygen-sensitive element 10. As can be seen in FIG. 3, the oxygen-sensitive element 10 in the sensor 30 is arranged such that the major surfaces of the plate-shaped substrate 12 (and accordingly the flat laminate of the concentration cell part 15) are perpendicular to the cross-sections of the cylindrical hood 36. The hood 36 has a length such that there is sufficient space therein between the unsupported end 10a of the oxygen-sensitive element 10 and the forward end 39, which is an open end in this example, of the hood 36. At a middle section between the forward end 39 and the forward end 10a of the element 10, the hood 36 is formed with two circumferential slits 37 which are symmetrical with respect to a plane containing the longitudinal axis of the hood 36 and perpendicular to the major surfaces of the substrate 12 of the element 10.

This oxygen sensor 30 is designed such that a major portion of the hood 36, that is, the portion on the left side of the line P—P in FIG. 2, intrudes into the interior of an exhaust manifold or an exhaust pipe with the longitudinal axis of the hood 36 directed generally perpendicular to the direction of the flow of exhaust gas at the location where the sensor 30 is installed.

Figure 4:
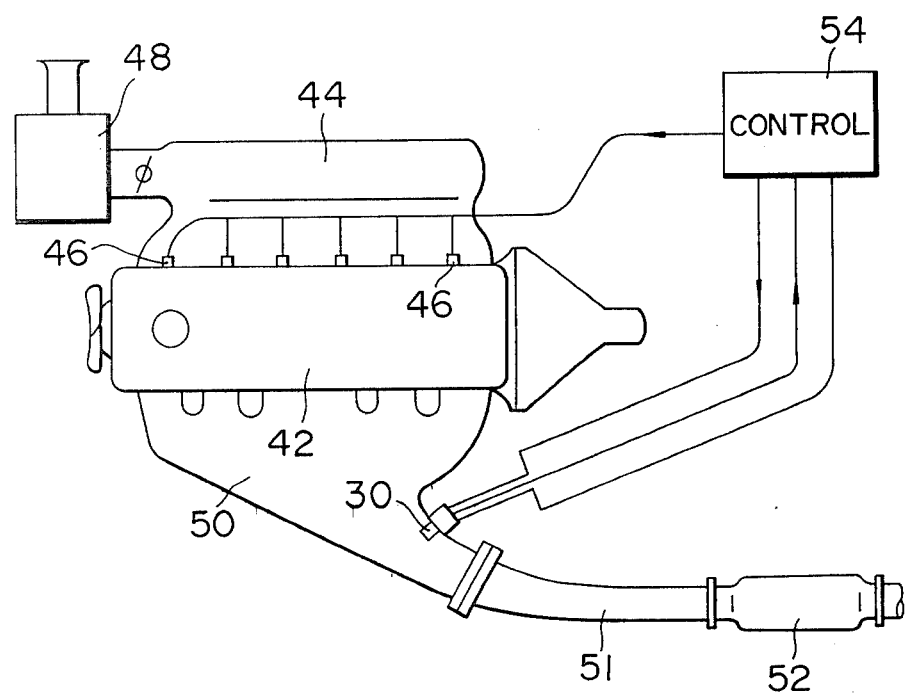
FIG. 4 is a diagrammatic illustration of an automotive internal combustion engine including an air-fuel ratio control system which utilizes an oxygen sensor of the invention to obtain a feedback signal.
Figure 5A:
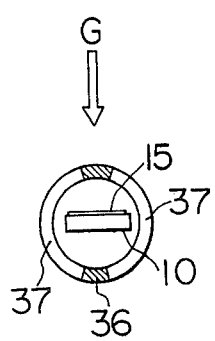
FIGS. 5(A), 5(B), 5(C) and 5(D) show respectively four different orientations of a sensitive part of the oxygen sensor of FIGS. 2 and 3 with respect to the direction of an exhaust gas flow in an exhaust manifold in FIG. 4 at a section where the oxygen sensor is disposed.
Figure 5B:
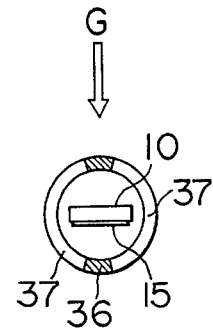
Figure 5C:
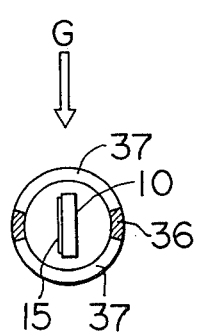
Figure 5D:
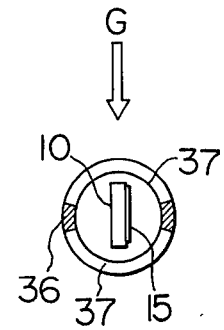

FIG. 4 illustrates the use of the oxygen sensor 30 of FIG. 2 in a system for feedback control of the air-fuel ratio in an automotive internal combustion engine 42. The engine 42 has a usual intake manifold 44 into which air is admitted through an air cleaner 48, electronically controllable fuel injection valves 46 and a usual exhaust manifold 50. Exhaust pipe 51 connects the exhaust manifold 50 to a catalytic converter 52 containing therein a conventional three-way catalyst for instance. As a component of the air-fuel ratio control system, the oxygen sensor 30 is attached to a downstream section of the exhaust manifold 50 such that the hood 36 is exposed to the exhaust gas in the manner as described above. The output voltage of this sensor 30 is representative of the content of oxygen in the exhaust gas and accordingly an actual air-fuel ratio of a gas mixture burned in the engine 42. To supply an optimal air-fuel mixture, in this case a stoichiometric mixture, to the engine 42 during its normal operation for thereby allowing the three-way catalyst in the converter 52 to exhibit its best conversion efficiencies, an electronic control unit 54 receives the output of the oxygen sensor 30 and provides a control signal to the fuel injection valves 46 based on the direction and magnitude of a deviation of the actual air-fuel ratio indicated by the output of the sensor 30 from the intended air-fuel ratio. The control unit 54 includes the function of supplying a heating current to the heater in the oxygen sensor and, where necessary, another DC current to the concentration cell part 15 of the sensor 30 to produce a reference oxygen partial pressure.

Turning again to FIGS. 2 and 3, a portion of the exhaust gas flowing in the exhaust manifold enters the interior of the hood 36 of the oxygen sensor 30 through one or both of the slits 37 (depending on the angular disposition of the hood 36 with respect to the direction of the flow of the exhaust gas). However, the exhaust gas flowing into the interior of the hood 36 does not directly collide against the oxygen-sensitive element 10 which is somewhat distant from the slits 37 in the direction longitudinal of the hood 36. The exhaust gas comes into contact with the major outer surface of the concentration cell part 15 after repeated collisions against, and reflections on, the inner surface of the hood 36 and/or the substrate 12 of the element 10. As the effects of such collision and reflection, the exhaust gas is well mixed and undergoes a considerable lowering in its flow velocity. Therefore, the oxygen-sensing function of the element 10 becomes almost independent of the orientation of the plate-shaped element 10 with respect to the angular positions of the slits 37 and the direction of the flow of the exhaust gas outside the hood 36. That is, the directionality of the plate-shaped oxygen-sensitive element 10 is compensated for by adequately spacing the gas inlet openings 37 of the hood 36 from the element 10.

Figure 6:
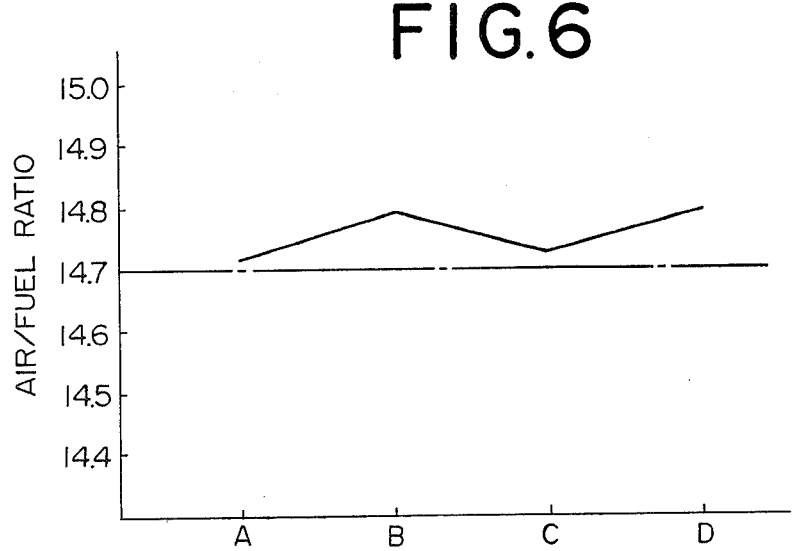
FIG. 6 is a chart showing variations in the performance of the air-fuel ratio control system observed when the orientation of the oxygen sensor of FIGS. 2 and 3 was varied as shown in FIGS. 5(A) to 5(D)

FIGS. 5(A) to 5(D) and FIG. 6 illustrate the result of an experiment on the oxygen sensor 30 of FIGS. 2 and 3 used in the air-fuel ratio control system of FIG. 4. The sensor 30 was attached to the exhaust manifold 50 at a definite section thereof in four different manners such that the orientation of the concentration cell part 15 of the oxygen-sensitive element 10 with respect to the direction of the flow of exhaust gas, indicated by arrow G, became as shown in FIGS. 5(A) to 5(D), respectively. In each case the engine 42 and the air-fuel ratio control system were operated for a predetermined period of time with the aim of maintaining a stoichiometric air-fuel ratio (14.7 by weight), and an actual air-fuel ratio at the end of the aforementioned time period was examined by analysis of sampled air-fuel mixture. The result of the analysis is shown in FIG. 6, wherein A, B, C and D on the abscissa represent the orientations of the oxygen-sensitive element 10 in FIGS. 5(A), 5(B), 5(C) and 5(D), respectively.

Considering the already known overall accuracy of the control system, the result in every case shown in FIG. 6 was judged to be satisfactory. Presumably the small difference in result between the case (C) and the case (D) is attributed to a deviation of the location of the slits 37 of the oxygen sensor 30 from the center of the exhaust gas stream in the exhaust manifold 50.

Figure 7:
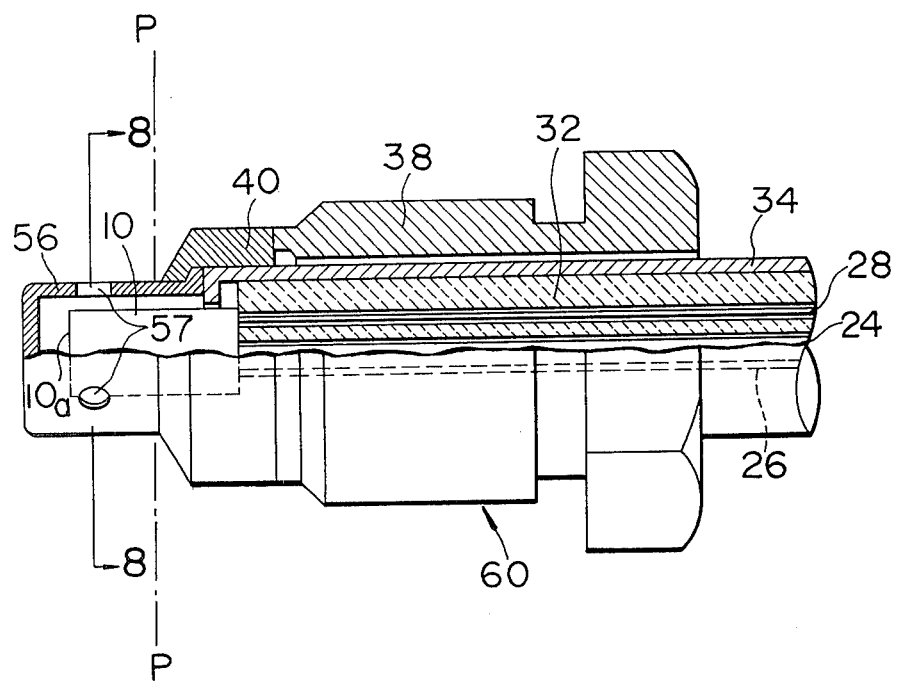
FIG. 7 is a partly sectional side elevation view of an oxygen sensor which resembles the sensor of FIG. 2 but is not in accordance with the invention.
Figure 8:
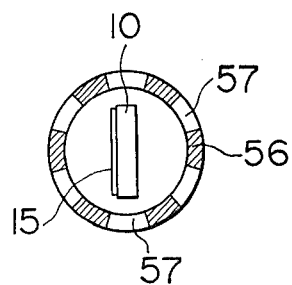
FIG. 8 is a cross-sectional view taken along the line 8—8 in FIG. 7.
Figure 9A:
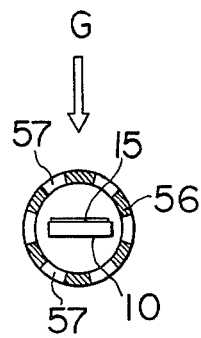
FIGS. 9(A), 9(B), 9(C) and 9(D) show the same matter as FIGS. 5(A) to 5(D) but with respect to the sensor of FIGS. 7 and 8.
Figure 9B:
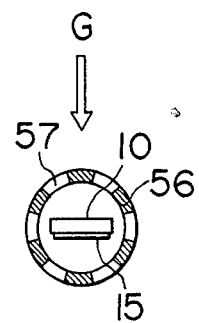
Figure 9C:
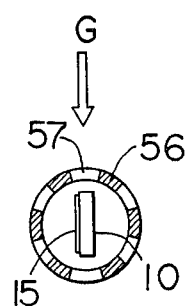
Figure 9D:
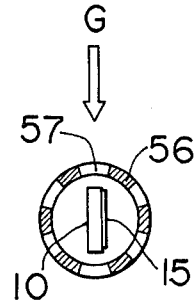

For the sake of comparison, FIGS. 7 and 8 show an oxygen sensor 60 which is almost identical with the sensor 30 of FIGS. 2 and 3 but is not in accordance with the present invention in the following one point. A hollow cylindrical hood 56 of this sensor 60, which corresponds to the hood 36 in FIGS. 2 and 3, is formed with six circular holes 57 at circumferentially equal intervals such that a gas flowing into the interior of the hood 56 through any of these holes 57 directly collides against the oxygen-sensitive element 10. In other words, a cross-sectional plane containing the centers of these holes 57 intersects the oxygen-sensitive element 10. Until now, this manner of arrangement of the gas inlet and outlet openings 57 in the hood 56 (whether the openings are in the form of circular holes or in the form of elongate slits) has been employed with a view to allowing the oxygen-sensitive element 10 to make a quick response to a change in the composition of the gas, but with little consideration of the directionality of the element 10.

Figure 10:
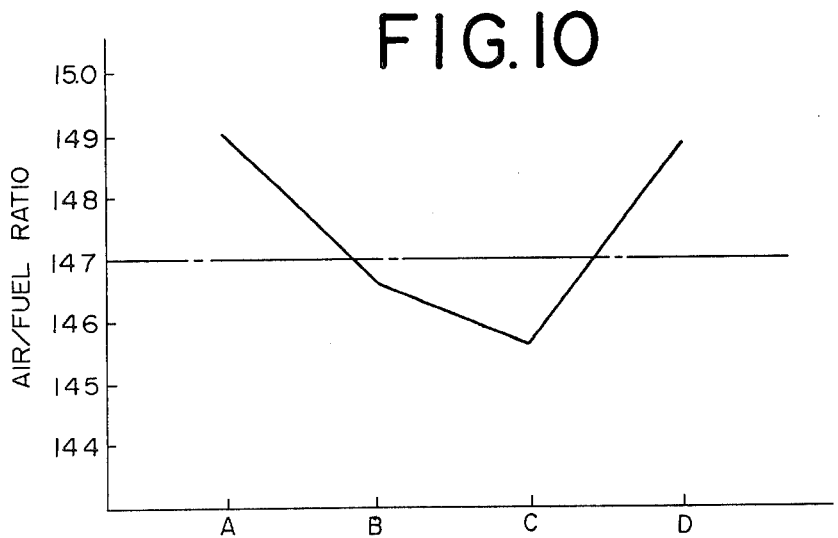
FIG. 10 is a chart showing the same matter as FIG. 6 but with respect to the orientations of the oxygen sensor shown in FIGS. 9(A) to 9(D)

The oxygen sensor 60 of FIGS. 7 and 8 was subjected to the above described experiment by varying the orientation of the oxygen-sensitive element 10 in the way as shown in FIGS. 9(A) to 9(D). The result of the analysis of sampled air-fuel mixtures is shown in FIG. 10, wherein A, B, C and D on the abscissa respresent the orientations of the oxygen-sensitive element 10 in FIGS. 9(A), 9(B), 9(C) and 9(D), respectively. This experimental result demonstrates that, in the case of using the sensor 60 of FIGS. 7 and 8, the performance of the air-fuel ratio control system significantly depends on the angular relation between the oxygen-sensitive element 10 in the sensor 60 and the direction of the flow of the exhaust gas. A remarkable effect of the present invention will be appreciated by comparing the graph of FIG. 6 with the graph of FIG. 10.

Figure 11:
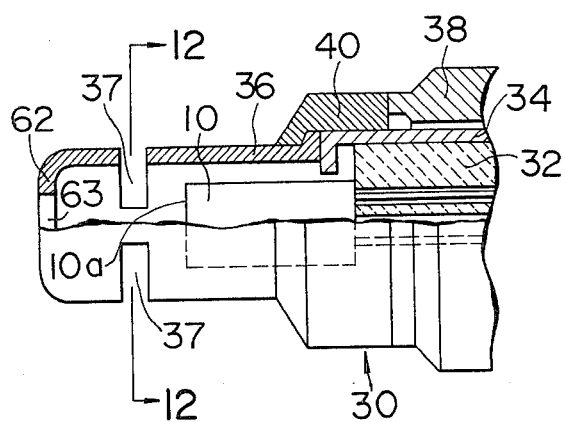
FIGS. 11 and 13 show respectively two kinds of modifications of the oxygen sensor of FIG. 2 in the same view.
Figure 12:
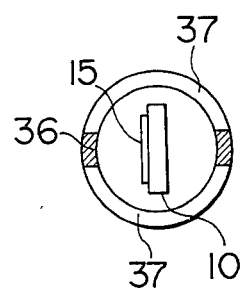
FIGS. 12 and 14 are cross-sectional views taken along the line 12—12 in FIG. 11 and along the line 14—14 in FIG. 13, respectively.

FIGS. 11 and 12 show a minor modification of the hood 36 of FIGS. 2 and 3. The slits 37 shown in FIGS. 11 and 12 are identical with the counterparts in FIGS. 2 and 3. The forward end of the hood 36 of FIG. 11 is not fully open as in FIG. 2 but takes the form of an annular wall 62 to leave a relatively small circular opening 63 in a central region. This modification does not produce a significant difference in the effects of the hood 36 though it can be said that a physical protective effect of the hood 36 on the oxygen-sensitive element 10 is slightly augmented.

Figure 13:
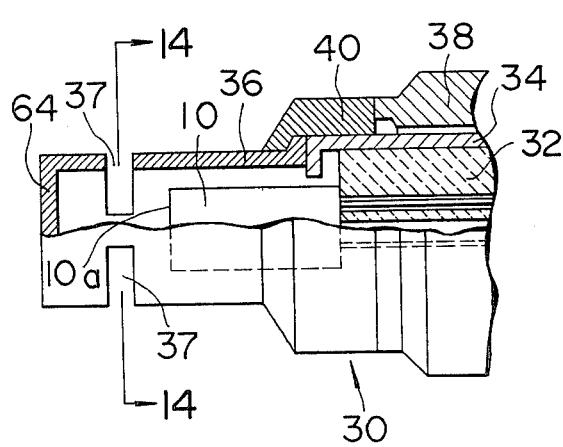
Figure 14:
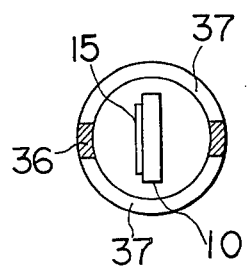

Referring to FIGS. 13 and 14, it is also possible to alter the annular wall 62 at the forward end of the hood 36 in FIG. 11 to a complete end wall 64 shown in FIG. 13 so that the exhaust gas can flow into the interior of the hood 36, and flow out, only through the circumferential slits 37. This modification contributes to further augmentation of the physical protective effect of the hood 36 and hence to prolongation of the service life of the oxygen-sensitive element 10.

Figure 15:
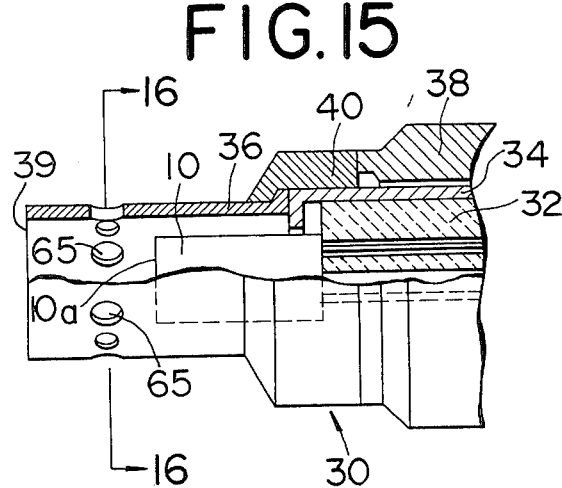
FIG. 15 is a partly sectional side elevation view of an oxygen sensor as a still different embodiment of the invention.
Figure 16:
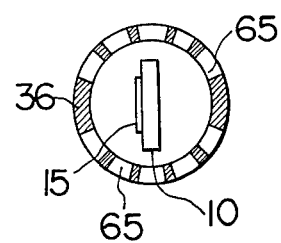
FIG. 16 is a cross-sectional view taken along the line 16—16 in FIG. 15.

FIGS. 15 and 16 show another modification of the hood 36 of FIGS. 2 and 3. In this case, each of the two arc-shaped slits 37 in FIGS. 2 and 3 is replaced by a plurality of circular holes 65 (five holes in the illustration) which are arranged circumferentially of the hood 36 at equal intervals. In the direction longitudinal of the oxygen sensor 30, these holes 65 are located forwardly of the unsupported end 10a of the oxygen-sensitive element 10. That is, a horizontal plane containing the centers of the holes 65 is distant from the end 10a of the element 10. Compared with the single elongate slit 37, the combination of the five holes 65 is more effective for well mixing the exhaust gas before its contact with the sensitive part 15 of the element 10 because of an enhanced tendency to turburence of the exhaust gas flowed into the interior of the hood 36 through the plurality of relatively small holes 65.

The total number of the above described holes 65 and the intervals between the holes 65 may arbitrarily be determined in consideration of the intended use of the oxygen sensor 30 or the physical properties of the sensitive element 10.

Figure 17:
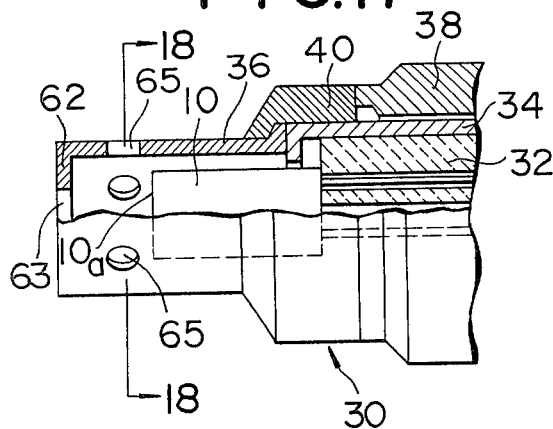
FIGS. 17 and 19 show respectively two kinds of modifications of the oxygen sensor of FIG. 15 in the same view.
Figure 18:
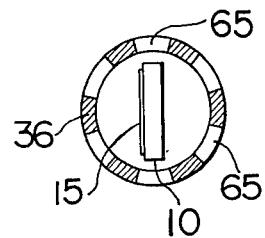
FIGS. 18 and 20 are cross-sectional views taken along the line 18—18 in FIG. 17 and along the line 20—20 in FIG. 19, respectively.
Figure 19:
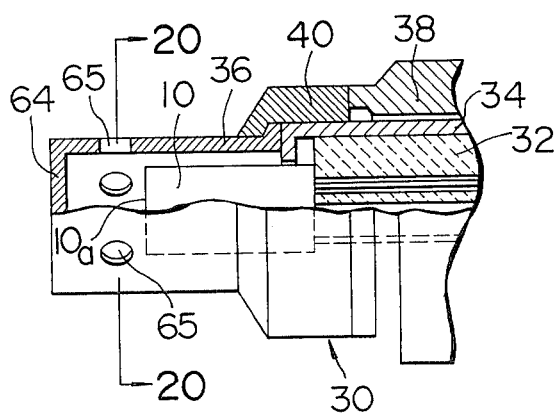
Figure 20:
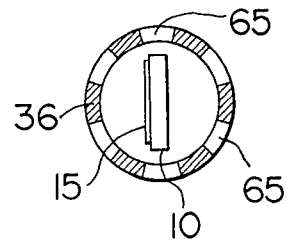

In FIGS. 17 and 18, the hood 36 is formed with six circular holes 65 arranged circumferentially at equal intervals. If desired, a plurality of holes represented by the holes 65 in FIGS. 15-18 may be formed at different distances from the forward end of the hood 36. As an additional modification, this hood 36 has an annular wall 62 at its forward end so as to leave a circular hole 63 in a central region similarly to the hood 36 in FIG. 11. As shown in FIGS. 19 and 20, the annular wall 62 in FIG. 17 may be altered to a complete end wall 64 as already described with reference to FIG. 13.

The foregoing description of the preferred embodiments of the invention have been presented for purposes of illustration and description. They are not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended thereto.

What is claimed is:

1. A gas sensor, comprising:
   a body adapted to be attached to an apparatus in which a gas subject to measurement flows;
   an oxygen sensitive element having a plate-shaped substrate fixed to an end portion of said body and a laminate comprising an inner electrode formed on a major surface of said substrate, an oxygen ion conductive solid electrolyte layer formed on an outer surface of said inner electrode layer, and an outer electrode layer formed on an outer surface of said solid electrolyte layer; and
   a generally hollow cylindrical hood having a cylindrical wall and an inner side and a free end, said hood being fixed to said body whereby said oxygen sensitive element is enclosed in said hood and entirely spaced from said inner side, said hood being formed with two arc-shaped slit type openings symetrically positioned in and extending circumferentially about said cylindrical wall to allow a portion of the gas flowing in said apparatus to flow into the interior of said hood and then flow out, each of said slit type openings being located between said oxygen sensitive element and said free end in a longitudinal direction with regard to a longitudinal axis of said hood whereby any cross-section of said hood taken in a plane generally perpendicular to said major surface of said substrate which intersects one of said slit type openings does not intersect said oxygen sensitive element;
   said substrate being fixed to said body such that said major surface of said substrate lies generally parallel to the longitudinal axis of said hood.

* * * * *